United States Patent [19]

Erickson

[11] 4,436,700

[45] Mar. 13, 1984

[54] AUTOCLAVABLE PIPETTE JAR AND METHOD OF USING IT

[75] Inventor: Eric D. Erickson, Lincoln, Nebr.

[73] Assignee: The Board of Regents of the University of Nebraska, Lincoln, Nebr.

[21] Appl. No.: 336,895

[22] Filed: Jan. 4, 1982

Related U.S. Application Data

[63] Continuation-in-part of Ser. No. 177,013, Aug. 11, 1980, abandoned.

[51] Int. Cl.³ .......................... A61L 2/00; A61L 2/26; B65D 25/00
[52] U.S. Cl. .................................. 422/102; 206/443; 220/70; 422/104; 422/300
[58] Field of Search ................. 422/102, 297, 300, 26, 422/104; 312/72, 73; 206/443, 445; 220/69, 70; 211/60 R, 2

[56] References Cited

U.S. PATENT DOCUMENTS

| | | | |
|---|---|---|---|
| 2,587,237 | 2/1952 | Sinaiko | 220/70 |
| 2,592,189 | 4/1952 | Rothrock | 211/60 R |
| 2,614,027 | 10/1952 | Kollsman | 422/297 |
| 2,736,449 | 2/1956 | Bruderer | 220/69 X |
| 2,881,947 | 4/1959 | Hancock | 211/60 R X |
| 3,288,318 | 11/1966 | Corbin et al. | 422/102 X |
| 3,474,929 | 10/1969 | Harker | 422/300 X |
| 3,814,522 | 6/1974 | Clark et al. | 356/197 |
| 3,971,491 | 7/1976 | Larssen et al. | 220/69 X |
| 4,139,093 | 2/1979 | Holmes | 206/445 X |

OTHER PUBLICATIONS

Fisher Scientific Company; Modern Laboratory Appliances, Catalog 63; 1962; p. 966.

Primary Examiner—Kenneth M. Schor
Attorney, Agent, or Firm—Vincent L. Carney

[57] ABSTRACT

To hold pipettes during autoclaving, an autoclavable pipette jar made of stainless steel has the general form of a closed cylindrical container with a flat generally disc-shaped base on one end and a flat top on the other end. Adjacent to the top is an opening in a portion of the curved wall to permit receiving and removing of the pipettes. One side of the generally disc-shaped base is cut away to form a straight resting surface. Also disclosed is a method of autoclaving the pipette jar with pipettes in it for sterilization.

6 Claims, 5 Drawing Figures

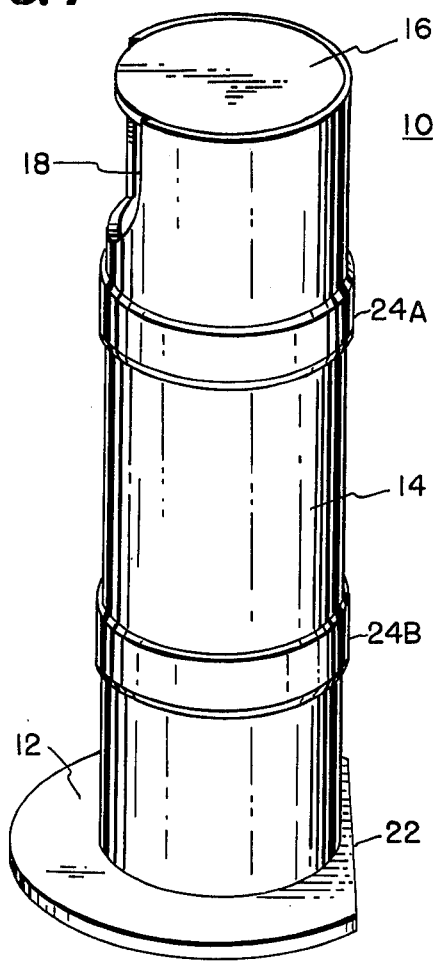
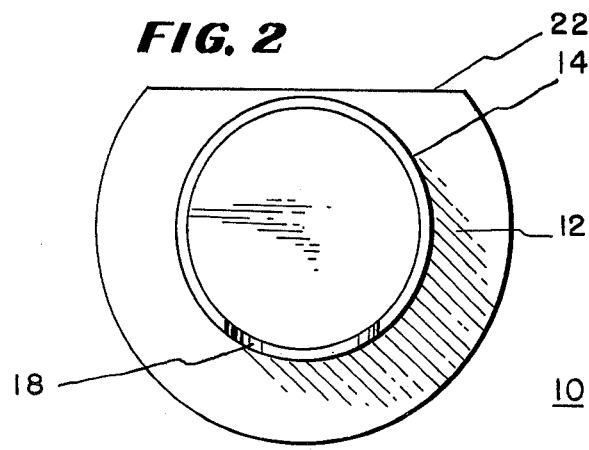
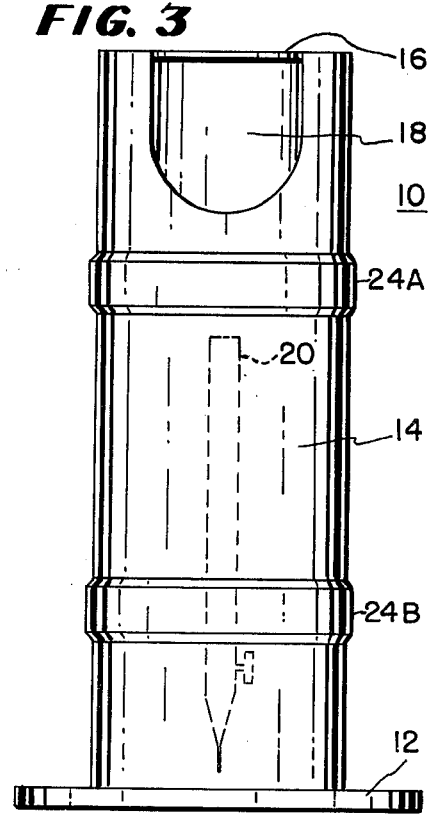
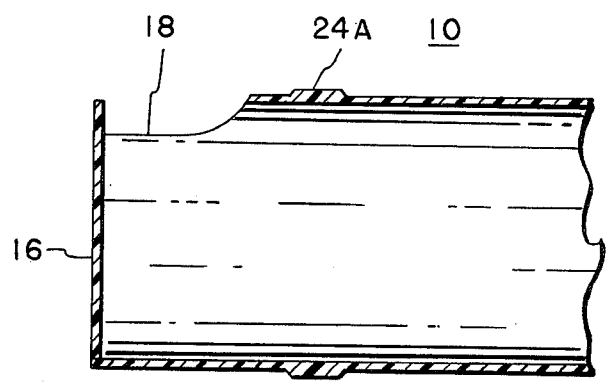
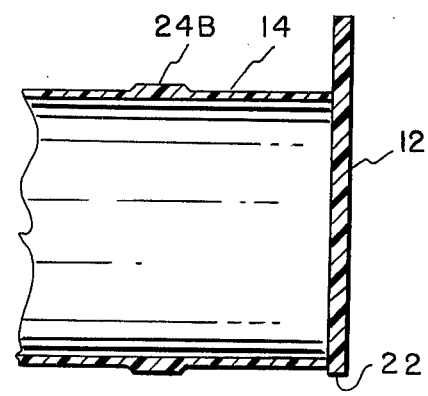

AUTOCLAVABLE PIPETTE JAR AND METHOD OF USING IT

REFERENCE TO RELATED APPLICATIONS

This application is a continuation-in-part application of U.S. application Ser. No. 177,013 now abandoned for AUTOCLAVABLE PIPETTE JAR filed by Eric Denis Erickson on Aug. 11, 1980 and assigned to the same assignee as this application.

BACKGROUND OF THE INVENTION

This invention relates to containers for sterilizing pipettes in a steam autoclave.

In one class of autoclavable container for sterilizing pipettes, the container is formed of a material that may be inserted into a steam autoclave. The pipettes are inserted into the container and the container and pipettes are placed in the autoclave and heated until sterile and then removed for use.

In one prior art type of this class of autoclavable container for sterilizing implements such as syringes, the container includes a multiple number of parts one of which is a removable top. After the top is removed, the implements are inserted and held in position by a perforated separator. The top is replaced and the implements are sterilized.

These prior art containers have a disadvantage in being complex and expensive because the container itself forms a part of the autoclave and the steam is generated within the container. Other autoclavable containers have the disadvantage of either: (1) not being long enough for some pipettes; or (2) if long enough to hold the pipettes, being too large to fit within some autoclaves.

Other classes of prior art autoclavable containers are known in which the pipettes or the like are held for cleaning or disinfecting with a solution but not for autoclaving. One such container is disclosed in U.S. Pat. No. 3,474,929 as an open wire container for holding disposable pipettes in a plastic bag. Others are closed plastic or metal containers adapted to have cleaning or rinsing fluids circulated through them.

These containers generally have the disadvantages of: (1) being complex; (2) not being able to heat sufficient water within them to a temperature that will sterilize the pipettes in a sufficiently short time; and (3) not be constructed of a size and shape to fit into steam autoclaves.

SUMMARY OF THE INVENTION

Accordingly, it is an object of the invention to provide an improved autoclavable jar.

It is a further object of the invention to provide an autoclavable jar which is of sufficient size to accommodate relatively large pipettes and yet may be autoclaved in different size autoclaves.

It is a still further object of the invention to provide an autoclavable implement jar which may be autoclaved in different positions within an autoclave.

It is still further object of the invention to provide a method of autoclaving by which pipettes may be sterilized in different positions within an autoclave depending upon the size of the pipettes.

In accordance with the above and further objects of the invention, an autoclavable pipette jar is tubular with a flat base on one end and top on the other. An opening is formed on the cylindrical wall adjacent to the top of the container, with the side walls, top and base being formed to permit the pipette jar to rest on its base or side and hold a liquid in either position.

In the preferred embodiment, the entire pipette jar is made of stainless steel but other autoclavable material may be used instead for all or part of it. The material or parts of it are advantageously capable of conducting heat to water in the interior of the container for increasing the temperature in a short time within an ordinary steam autoclave and the container must be capable of holding the heated water until the pipettes within the container are sterile.

In one embodiment, the base advantageously extends beyond the tubular wall to form a shoulder and has a straight edge so that the container may rest either on its side supported by the flat edge or on its base.

The pipette container may be used in more than one mode. In each mode, the pipette container with pipettes in it is inserted in a standard steam autoclave which increases the temperature and pressure until the interior is 121 degrees Celsius. The container is constructed to permit the temperature within the container to reach 121 degrees centigrade preferably at least within one hour after the autoclave reaches this temperature. Normally, the steam autoclave requires several minutes, such as fifteen minutes, to reach this temperature and another several minutes to cool.

In one mode of operation, the pipettes are place into the pipette container while the container is upright and then soaked with water or a water-disinfectant solution. Usually, the container is filled first with the solution and then the pipettes inserted into the container so that the pipettes are filled with the liquid as they pass into the container. In another mode, the pipettes are inserted while the container is resting on its side and filled with solution, and in still another mode, no liquid is put into the container at all before autoclaving.

When the contents of the container are to be autoclaved, the container is inserted into a steam autoclave. If the container is too large to fit upright within the steam autoclave, it may be placed on its side so as to rest against the flat edge to prevent rolling. If no liquid has been inserted into the container before autoclaving, after autocalving, the pipettes within the autoclave are removed and acid-cleaned to remove any residue that may have adhered onto the pipettes during autoclaving without a liquid.

As can be understood from the above description, the autoclavable pipette jar and method of this invention has several advantages such as: (1) it is relatively inexpensive; (2) it may be autoclaved with several pipettes within it; (3) it may be positioned in either of two positions within an autoclave so that it may fit within different size autoclaves even though it may hold relatively large size pipettes; (4) it may be used for several modes of autoclaving; and (5) pipettes may be placed into the jar in the vertical or horizontal position so as to permit easy use within biosafety cabinets.

SUMMARY OF THE DRAWINGS

The above noted and other features of the invention will be better understood from the following detailed description when considered in connection with the accompanying drawings in which:

FIG. 1 is a perspective view of an autoclavable pipette jar in accordance with an embodiment of the invention;

FIG. 2 is a top view of the embodiment of FIG. 1;

FIG. 3 is a side elevational view of the embodiment of FIG. 1;

FIG. 4 is a longitudinal sectional view through the embodiment of FIG. 1; and

DETAILED DESCRIPTION

Figure 5:
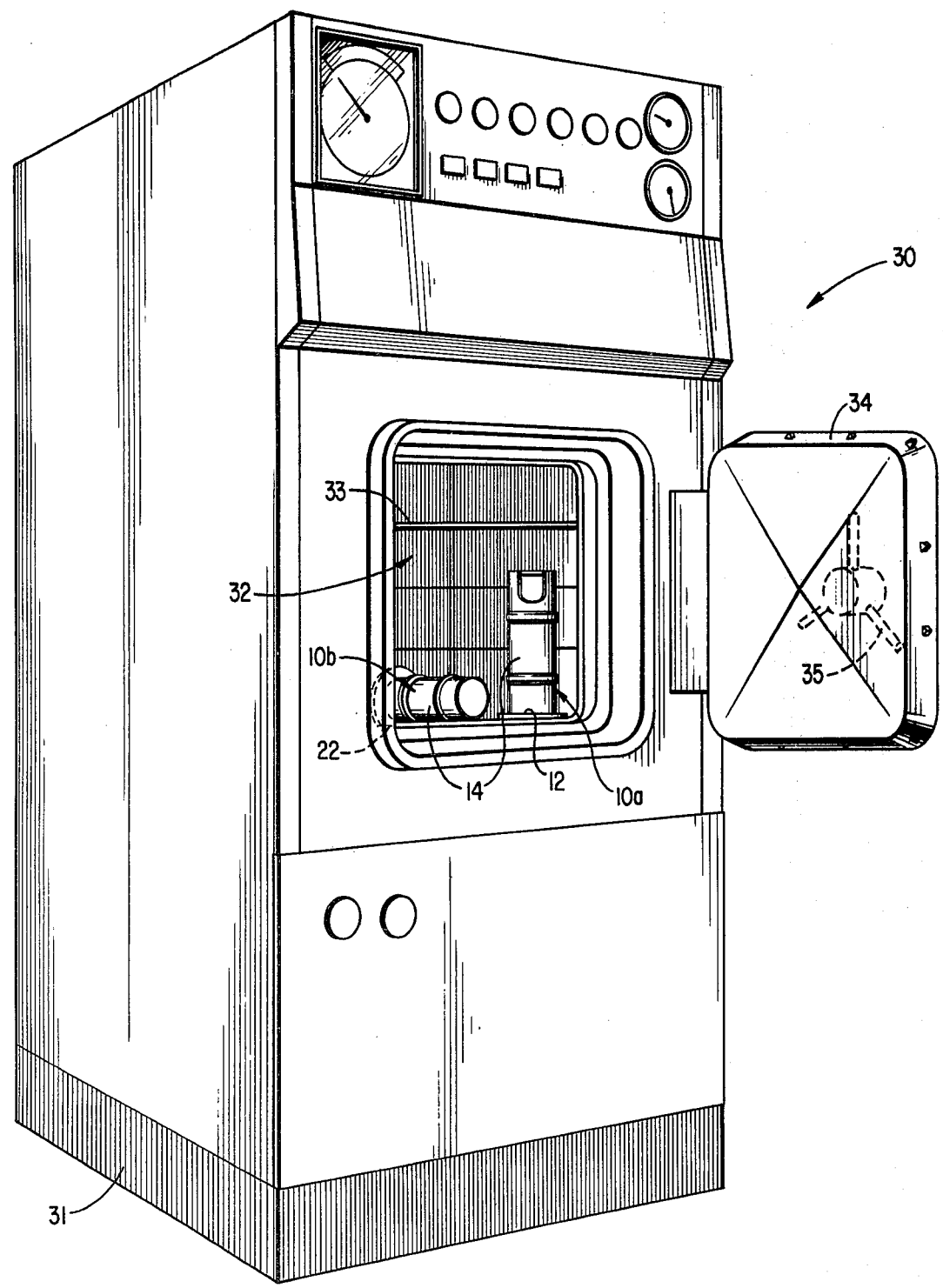
FIG. 5 is a perspective view of a typical autoclave with which the autoclavable pipette jar of the present invention may be employed.

In FIG. 1, there is shown a perspective view of an autoclavable pipette jar 10 formed generally as a cylindrical enclosure and having as its principal parts a disc-shaped base 12, a cylindrical side wall 14, a top wall 16 and an opening 18. The disc-shaped base 12 is concentric and extends beyond the cylindrical side wall 14 to which it is orthogonal. It includes an annular shoulder partly circumscribing the cylindrical side wall 14 and a straight edge 22 that is perpendicular to a radius of the cylindrical side wall 14 which radius bisects it.

The cyindrical side wall 14 is centered in the disc-shaped base 12 so that one side is close to the straight edge 22 and the remainder is equidistant from the edge of the disc-shaped base 12. The cylindrical side wall 14 should be self-supporting and closed against the disc-shaped base 12 to form a liquid holding container.

The disc-shaped base 12 is approximately one-half of an inch in height and has a diameter of approximately twelve and one-quarter inches except for the straight edge 22. The straight edge 22 is approximately eight inches long. The cylindrical side wall 14 has an outer diameter of approximately six inches and rises upwardly from the flat side of the disc-shaped base 12 for approximately twenty inches to accommodate relatively long pipettes such as that shown at 20 (FIG. 3) in an upright position within the cylindrical side wall 14. Two spaced-apart rings 24A and 24B circumscribe it.

The disc-shaped base 12 is sufficiently large to support the autoclavable pipette jar 10 in its upright position. For containers formed with a cylindrical compartment having a ratio of diameter to height that is sufficiently large to support the container stably in an upright position, the annular shoulder is unnecessary and a projection on one side that has a straight edge supports the container on its side in a stable position is sufficient. For containers with a smaller ratio of cylinder diameter to height, the annular shoulder and straight portion should be large enough to stabilize the container in an upright position. The straight edge of the disc-shaped base 12 should be long enough to stably support the container so as to prevent it from rolling when on its side. Prototypes have been designed by others for consideration by the inventor in which a square removable flanged base is used for vertical stability and flat sides are used for horizontal stability.

The cylindrical side wall 14 in the embodiment of FIG. 1 is closed at the bottom by the disc-shaped base 12 and at the top by top wall 16. There is one opening into its interior in the cylindrical side wall 14 adjacent to the top wall 16 which forms an opening curved at its bottom and flat at its top where it intersects the top wall 16. It is of sufficient size to receive pipettes. A door may be used to close this opening for moving the pipette jar from place to place.

In the preferred embodiment, the bottom-most portion of the opening is four inches down from the top wall 16. The cylindrical side wall 14 is approximately one-eighth of an inch thick but the thickness of the walls is selected to permit adequate strength and heat conductivity.

In FIG. 2 there is shown a bottom view of the autoclavable pipette jar 12 having the straight edge 22 in the disc-shaped base 12 positioned opposite to the opening 18. As best shown in FIG. 3, the autoclavable pipette jar 10 may rest on the disc-shaped base 12 which supports the autoclavable pipette jar 10 with the opening 18 upward (FIGS. 1, 3 and 4).

As best shown in FIGS. 3 and 4, the autoclavable pipette jar 10 may rest in either of two positions on the floor of the autoclave or biosafety cabinet, which are: (1) upright, resting on its disc-shaped base 12; or (2) on one side, with the straight edge 22 against the supporting floor of the autoclave or biosafety cabinet. In each position, the pipettes are insertable through the opening 18 and the opening 18 faces upwardly. The autoclavable pipette jar 10 will hold a liquid for cleaning purposes in either position.

A typical autoclave with which the present invention may be employed is a steam autoclave in the form of a vertical vessel 30, as shown in FIG. 5, having dimensions such as a rectangular base 31 of about 35×45 inches and a height of about 72 inches, for example. Such autoclaves are well known in the art to which the invention pertains.

The interior chamber 32 of a typical steam autoclave 30 has dimensions such as, for example, about 16×16×24 inches. The interior chamber 32 is generally provided with racks or shelves 33 for holding materials to be sterilized and the door 34 which provides access to the interior chamber 32 may be manually operated by means such as a handle 35 in combination with a mechanical lock (not shown) which prevents opening of the door 34 until pressure within the interior chamber 32 has been released.

The steam autoclave 30 has a larger interior chamber 32 for purposes of illustration. A pipette jar will not fit vertically in a typical 16×16×24 inch compartment.

Such steam autoclaves 30 are usually connected directly to the steam supply of the building in which they are located, such as 40–60 psi steam lines. Initial heat-up time is about 8 to 15 minutes. Sterilizing temperatures obtained within the steam autoclave 30 are generally in the range of about 212 degrees to about 350 degrees F.

Before inserting the autoclavable pipette jar 10 into an autoclave, it is used to hold pipettes or other implements which are to be sterilized. In one mode of operation, it is also utilized to aid in cleaning the pipettes or other implements.

In one mode of use, the autoclavable pipette jar 10 rests on its disc-shaped base 12 while the pipettes 20 are soaked in a liquid within it. The liquid may be inserted first and then the pipettes lowered into the liquid or the pipettes may be inserted first and the liquid applied later, although the former method is normally used so that the autoclavable pipette jar 10 may accumulate pipettes in a liquid disinfectant solution for later sterilization within an autoclave.

In some laboratories, it is preferred to rest the autoclavable pipette jar 10 on its back as shown in FIG. 4 and soak the pipettes 20 in this position. This is done to reduce the formation and bursting of bubbles which may contain pathogenic materials such as bacteria as the pipette is filled which bursting may spread the pathogen and may be done in a biosafety cabinet. By utilizing the container in its flat position, the problem of spreading bacteria and the like is reduced.

In still another mode, the pipettes 20 are inserted and autoclaved in the container without a solution. In this mode, after autoclaving, the pipettes 20 or other implements are generally acid-cleaned to remove material which may have adhered to them during autoclaving.

Because the autoclavable pipette jar 10 may be filled with a liquid which it is resting on its side as shown in FIG. 4 and then raised to an upright position for autoclaving or filled when it is in its upright position as shown in FIG. 3 and then inserted into the autoclave in a side position such as shown in FIG. 4 to accommodate the size of the autoclave, the opening 18 should be dimensioned in such a fashion that, when filled with a liquid while on its side up to the opening 18 and then raised to its upright position, the liquid level is below the opening 18 in its upright position and when it is filled with a liquid in its upright position such as FIG. 3 and lowered on its side the liquid level is below the opening 18. This factor limits the depth of the opening 18 in each position.

In the sterilization of implements such as pipettes in the steam autoclave 30, one or more pipettes are inserted through the opening 18 of the autoclavable pipette jar 10 of the present invention. The autoclavable pipette jar 10 is then placed inside the interior chamber 32 of the steam autoclave 30. Depending on the size of the autoclavable pipette jar 10 relative to the interior chamber 32, the autoclavable pipette jar 10 may be placed upright, as shown at element 10a in FIG. 5, resting on its disc-shaped base 12. Alternatively, the autoclavable pipette jar 10 may be placed on one side, as shown at element 10b, thus resting on the straight edge 22 and a portion of the cylindrical side wall 14.

The door 34 of the steam autoclave 30 is then secured and steam is admitted to the interior chamber 32 until its temperature and corresponding pressure is at least 121 degrees Celsius for the purpose of sterilizing the pipettes. After a suitable interval at that temperature for sterilization, which should be less than one hour, the autoclavable pipette jar 10 with pipettes stored therein may be removed from the interior chamber 32, and the sterilized pipettes withdrawn from the autoclavable pipette jar 10 through the opening 18.

The autoclavable pipette jar 10 may be made of any autoclavable material. The preferred embodiment is constructed of stainless steel. Polypropylene is also possible, but because of its insulative qualities, the autoclavable pipette jar 10 must contain portions of better heat conductive materials such as stainless steel or it would have to remain in the autoclave for an extended period of time.

The material of which the side walls and bottom or a portion of them should be of sufficiently high conductivity to permit the inside of the autoclave to be rapidly heated to 121 degrees Celsius and preferably within one hour after the autoclave reaches 121 degrees Celsius. In many applications, this time is fifteen to thirty minutes. Preferably, a metal should be used for the jar 10 with a coefficient of thermal conductivity of less than one calorie per centimeter-second degree-Celsius. Materials which have thermal coefficients within the hundreds are not suitable if the entire unit is made of them and the autoclavable pipette jar 10 should contain a substantial portion with a thermal conductivity coefficient of less than 100.

With this construction, the autoclavable pipette jar 10 may be autoclaved with pipettes in it for sterilization either in the upright position or on its side without damage to the material.

While the autoclavable pipette jar 10 has a cylindrical side wall 14 and a disc-shaped base 12 with a straight edge 22 to enable it to be supported in either of two positions for convenient fitting within different size autoclaves, other configurations are possible to permit such use, but it is important that there be surfaces adapted to support the autoclavable pipette jar 10 in two positions at an angle to each other, each of which holds the opening 18 at an upper position.

From the above descriptions, it can be understood that the autoclavable pipette jar 10 of this invention has several advantages such as being able to fit within different size autoclaves and biosafety cabinets because of its ability to assume different positions, its easy reception in removal of pipettes in either position and its ability to be autoclaved without damage.

Although a preferred embodiment has been described with some particularity, many modifications and variations of the invention are possible in the light of the above teachings. Therefore, it is to be understood that, within the scope of the appended claims, the invention may be practiced other than as specifically described.

What is claimed is:

1. A two-position autoclavable container comprising:
walls of autoclavable material forming a compartment for holding pipettes;
said walls of autoclavable material being shaped to form a base, a side wall and a top of said container with the base, side wall and top at least partly defining and enclosing said compartment;
said base having a flat bottom surface, whereby said container may be supported thereon in a first stable position;
said side wall being tubular and extending upwardly from said base;
constraint means for preventing said container from rolling when it rests in a second stable position where it is not supported by the flat bottom surface, whereby said container may be supported in the second stable position and wherein said constraint means includes a straight resting edge which extends as a side of said base, with the base being otherwise generally disc shaped;
said base, side wall and top having a continuous portion, whereby said pipette jar may hold a liquid when resting in either said first or said second stable position; and
said side wall having an opening immediately adjacent to said top and located on the opposite side of said compartment from said straight resting edge, whereby said opening is near the top of said compartment and pipettes can be inserted through said opening with said container resting in a selected one of said first or said second stable positions to permit said container to be placed in an autoclave in either of said two positions while holding a liquid.

2. A two-position autoclavable container in accordance with claim 1 in which said constraint means includes at least one straight resting edge on said base and one other point on said side wall spaced from said one straight resting edge in the direction of said top, whereby said container is supported by said straight resting edge and one other point against tipping in a position to hold a liquid.

3. A two-position autoclavable container in accordance with claim 2 in which:
   said tubular wall is cylindrical and has its longitudinal axis extending orthogonally toward the flat bottom surface of said base;
   said base being generally disc shaped with said one straight edge;
   the cylindrical tubular wall has a dimension along said longitudinal axis longer than any other dimension; and
   the ratio of the diameter of said base to the height of the container being sufficiently large to support the container stably in an upright position.

4. A two-position autoclavable container in accordance with claim 3 in which said straight edge is perpendicular to a radius of said disc-shaped base and said radius bisects said straight edge.

5. A two-position autoclavable container in accordance with claim 1 in which:
   said tubular wall is cylindrical and has its longitudinal axis extending orthogonally toward the flat bottom surface of said base;
   said base being generally disc shaped and having one straight edge;
   the cylindrical tubular wall has a dimension along said longitudinal axis longer than any other dimension;
   and
   the ratio of the diameter of said base to the height of the container being sufficiently large to support the container stably in an upright position.

6. A two-position autoclavable container in accordance with claim 5 in which at least some parts of said walls are formed of a heat conductive material having a coefficient of conductivity less than 100 calories per centimeter-second-degree Celsius.

* * * * *